United States Patent [19]

Nunamaker et al.

[11] Patent Number: 4,604,996

[45] Date of Patent: Aug. 12, 1986

[54] EXTERNAL SKELETAL FIXATOR

[76] Inventors: David M. Nunamaker, 396 Valley Rd., West Grove, Pa. 19390; Dean W. Richardson, 1291 New London Rd., Landenberg, Pa. 19350

[21] Appl. No.: 710,376

[22] Filed: Mar. 11, 1985

[51] Int. Cl.$^4$ .............................................. A61F 5/04
[52] U.S. Cl. ................................ 128/87 R; 128/92 R; 119/96; 54/82
[58] Field of Search ............... 128/87 R, 92 R, 92 A, 128/92 B, 93; 119/96, 127; 54/80, 82

[56] References Cited

U.S. PATENT DOCUMENTS

| | | | |
|---|---|---|---|
| 2,825,329 | 3/1958 | Caesar | 128/92 R |
| 3,470,873 | 10/1969 | Walker et al. | 128/88 |
| 3,877,424 | 4/1975 | Murray | 128/92 A |
| 4,029,090 | 6/1977 | Dawson | 128/87 R |
| 4,099,525 | 7/1978 | McCarthy | 128/87 R |
| 4,320,722 | 3/1982 | Glassman et al. | 119/96 |
| 4,360,012 | 11/1982 | McHarrie et al. | 128/92 A |
| 4,502,473 | 3/1985 | Harris et al. | 128/92 R |

*Primary Examiner*—Gene Mancene
*Assistant Examiner*—John G. Weiss
*Attorney, Agent, or Firm*—Richard L. Hansen

[57] ABSTRACT

An external skeletal fixator for treating an injured mammalian limb, such as a horse's foreleg, includes a plurality of transfixation pins which transfix the bone at separated sites along the limb proximal the injury and terminate beyond the limb; means, exemplified by an organic polymer, for rigidly connecting pin terminii to a weight bearing member carried beneath the foot of the limb; together with means, e.g., affixing said weight bearing member to the foot of the limb, for immobilizing the limb distal the injury, whereby the weight of the mammal is transferred from the limb proximal the injury to the weight bearing member, permitting the mammal to ambulate while the injury heals.

20 Claims, 7 Drawing Figures

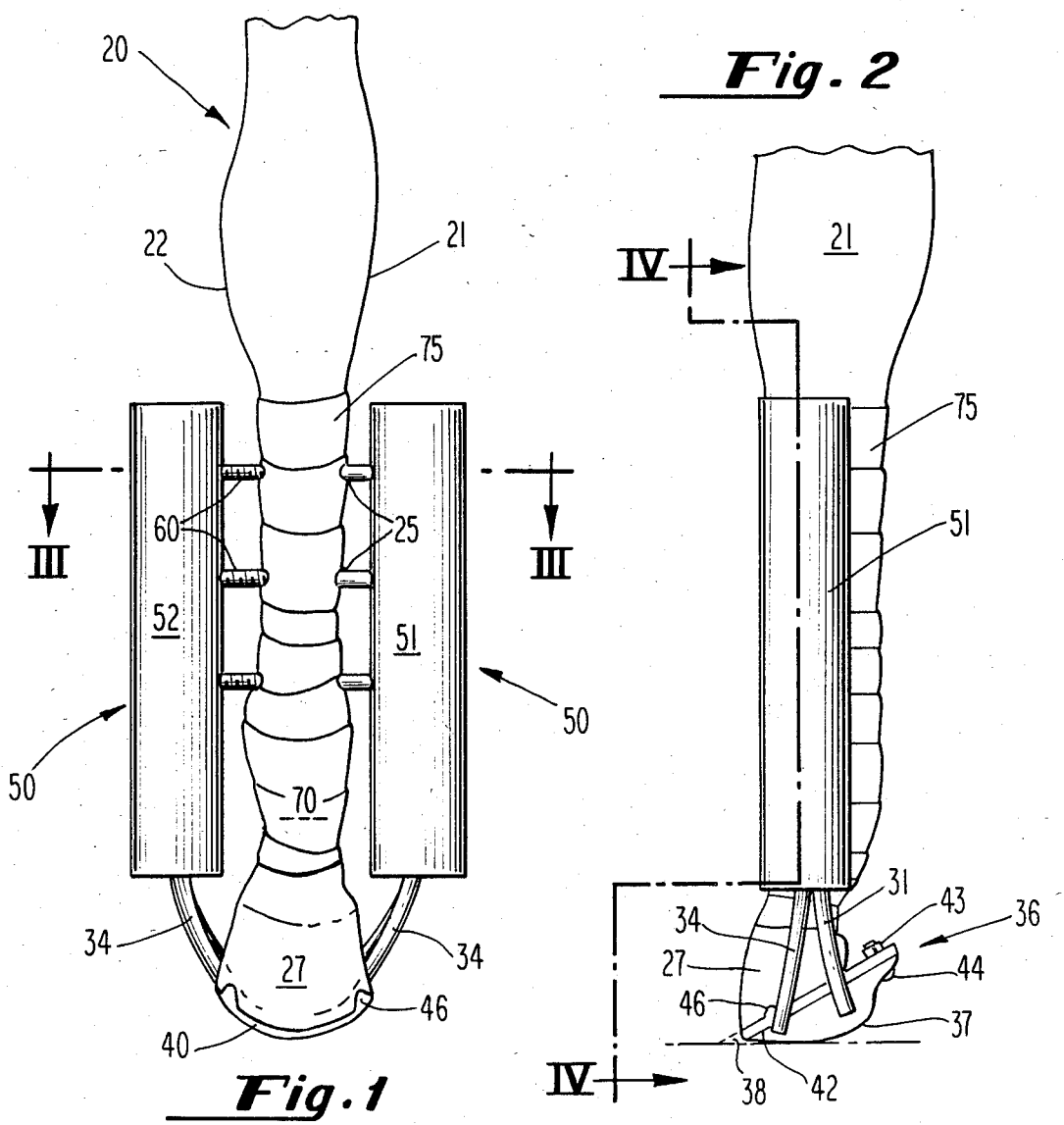
Fig. 2
Fig. 1
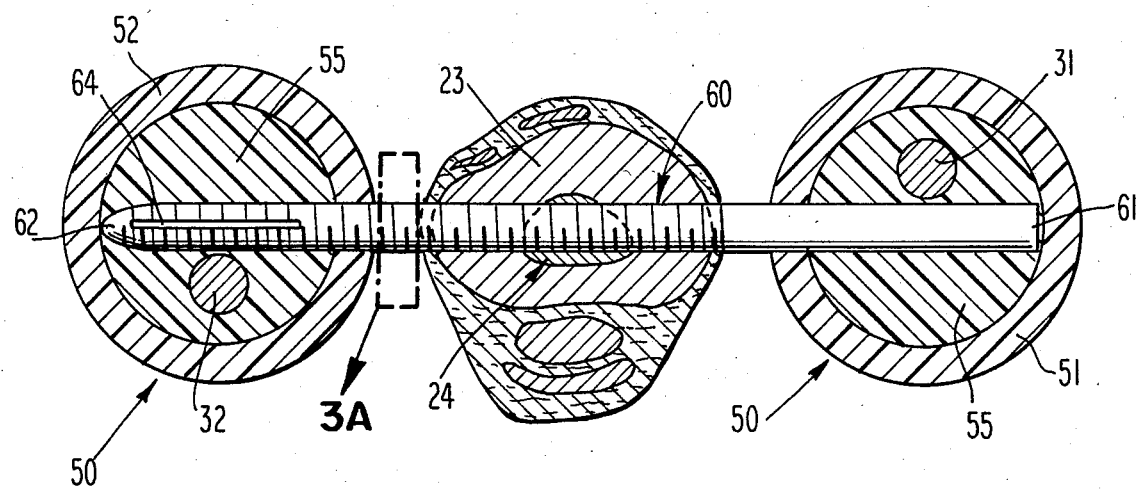
Fig. 3

EXTERNAL SKELETAL FIXATOR

This invention is in the field of apparatus and methods for treating injuries to the bones and soft tissues of mammalian extremities; more particularly, it relates to the use of external skeletal fixators for immobilizing the extremities while permitting full weight bearing on the injured limb.

Injuries to the limbs of mammals, including animals and man, are generally treated by immobilizing the limb until the injury heals. Application of a cast, brace or splint is nearly axiomatic in the case of fractures of legs and arms, or when soft tissues in these limbs have been severely bruised or strained. Whereas immobilization of the extremity is the treatment of choice for such injuries, encasing the limb in one of these appliances presents several disadvantages.

In the first place, the injured limb is often swollen, and the skin may be broken. Application of such a device puts painful pressure on the injured area initially, and then, as the injury mends, the device no longer supports the limb when the swelling recedes. Secondly, cuts and open wounds, often associated with such injuries, cannot be treated without removing the appliance, and its replacement after attending to these problems adds additional expense to the treatment. In addition, plaster casts are notoriously heavy and cumbersome, as well as uncomfortable and prone to soiling, making their presence especially unpleasant for the patient. If the patient happens to be an uncooperative animal, the appliance may be twisted, bent or broken in attempts to use the limb, complicating the injury.

A number of solutions have been proposed purporting to overcome the problems associated with using old fashioned casts, braces and spints to immobilize injured limbs. For example, Walker, U.S. Pat. No. 3,470,873, discloses an adjustable splint which is said to be especially useful to immobilize the injured leg of a bovine animal. The Walker splint includes a pivoting plate, to which the foot of the animal is attached, and the animal can walk about with the splint in place. Dawson, U.S. Pat. No. 4,029,090, describes a heavy, hinged framework which can be employed to encase the injured foreleg of a horse. Application of the brace allows the horse to stand but causes rub sores. A simple brace for an equine animal's injured leg, including a support for the hoof, is disclosed in U.S. Pat. No. 4,320,722 to Glassman, et al.

All of the aforesaid devices, like a plaster cast augmented with crutches, support the entire weignt of the mammal on soft tissues. This is undesirable. The soft tissue is subject to abrasion from the device, causing open sores to develop, as well as bruising. These painful consequences discourage ambulation. On the other hand, it is well known that exercising the limb is beneficial to healing, and this is especially the case for equine animals.

It has been proposed to treat fractured limbs by immobilization, not with soft tissue constraint, but with external fixation of the bone; see Murray, U.S. Pat. No. 3,877,424. In the technique disclosed by Murray, pins are inserted through the bone fragments and extend beyond the surrounding soft tissue, where they are bonded to a rigid bridge. Although the Murray fixator overcomes a number of the problems associated with earlier limb immobilization techniques, the Murray fixator makes no provision to allow full weight bearing on the injured limb so as to encourage or permit ambulation.

Thus, it is one object of this invention to provide apparatus and a method of using it which are effective for treating an injured mammalian limb, while avoiding the problems recited above. It is another objective that the treated limb be capable of supporting the mammal's full weight immediately after application of the apparatus without reliance on soft tissue support. Other objectives will become apparent hereinafter.

In attaining these objectives this invention provides an external skeletal fixator which includes a plurality of transfixation pins which transfix bone at separated sites along the limb proximal the injury and terminate beyond the limb; means for rigidly connecting pin terminii to a weight bearing member carried beneath the foot of the limb; together with means for immobilizing the limb distal the injury. By its use, the invention allows the weight normally borne on the injured limb to be transferred from the transfixed bone proximal the injury to the weight bearing member beneath the foot, bypassing the injury, and permitting the mammal to ambulate or otherwise use the limb while the injury heals. While healing takes place, the limb can be readily examined and treated without disrupting the appliance.

Although the apparatus and method of this invention are equally applicable to man and animals, the invention finds special utility when employed to treat animals, since all four limbs typically bear the animal's weight. Among the various animals, those members of the equine family, e.g., horses which suffer leg injuries, are perhaps benefited the most by the invention.

The invention will be clarified by reference to the drawings which accompany this specification and illustrate preferred embodiments and optional features and to the detailed description which follows.

In the drawings:

FIG. 1 is a front view of a horse's left foreleg having an injured pastern bone treated with one embodiment of the external skeletal fixator of this invention.

FIG. 2 is a right side view of the foreleg and fixator of FIG. 1.

FIG. 3 is a cross-sectional view taken along the line labeled III—III in FIG. 1.

Figure 4:
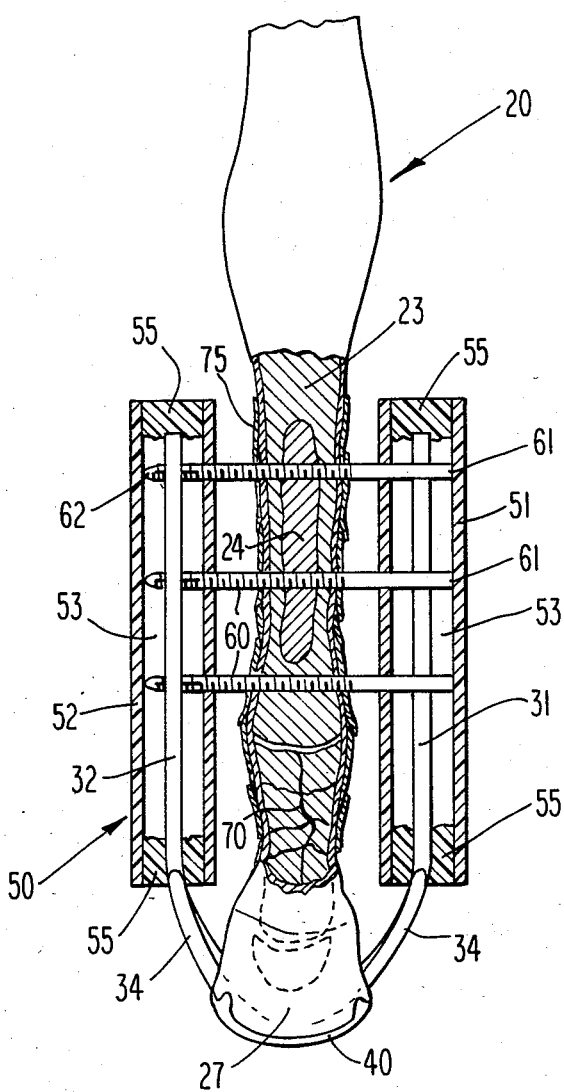
FIG. 4 is a cross-sectional view taken along the line labeled IV—IV in FIG. 2, but omitting portions of rigid organic polymer 55 to more clearly shown the elements.

With reference to the drawings, injured limb 20, characterized by lateral side 21, medial side 22, bone 23, hoof 27, and an injury 70, is treated with apparatus according to the method of this invention. In place on the injured limb, the apparatus includes transfixation pins 60, which transfix bone 23 proximal the injury and terminate beyond the limb on lateral side 21 and medial side 22. Weight bearing member 36 is carried beneath hoof 27. Sidebars 50 include preferred means for rigidly connecting pin terminii 61 and 62 to the weight bearing member.

The transfixation pins 60 can take several forms. The pins will vary, of course, in both size and number depending upon the particular injury being treated and will be made of a material, such as implant grade or 316L stainless steel, which is impervious to degradation in the mammalian body and should not break, loosen in the bone, or undergo deflection. In sizing the pins and deciding on the number to be transfixed proximal the injury, it is necessary to consider the weight of the mammal, the diameter of the bone, and the weakening of the bone due to the pins passed through it.

In the aggregate, the pins proximal the injury must support the full weight of the mammal with a comfortable safety margin and without deflection. It is known that holes up to about 30 percent of their diameter can be drilled through a bone without catastrophic failure. Pin bending strength is proportional to the fourth power of the pin diameter, while pin deflection is proportional to the cube of the distance between the outer cortex of the bone and the point at which the pin terminus is rigidly connected. With these considerations in mind, the number of pins, their diameter, and their length can be readily determined for a given case. In addition to the transfixation pins shown in the drawings, additional smaller pins or screws can be used to control bone fragments or otherwise reduce the injury, and these can be incorporated into the apparatus along with the illustrated pins.

Figure 3A:
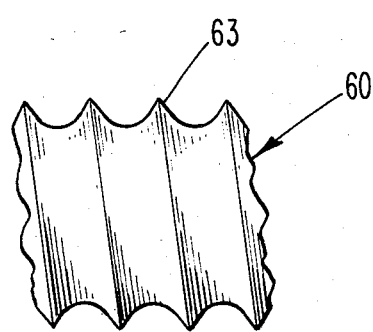
FIG. 3A is an enlarged fragmentary view of the enclosed area designated 3A in FIG. 3.

A preferred embodiment of transfixation pin 60 appears in FIGS. 3 and 3A. The pin is threaded from tapered end terminus 62 to a point beyond the middle of the pin, the head end terminus 61 then being of larger core diameter. Thread 63 is preferably cut with a rounded tool to reduce the stress concentration associated with a V-shaped cut. One or more flutes 64 are cut to make the pin self-tapping. Both the taper and the flutes are outside the point of rigid connection of the pin to sidebar 50, so the effective diameter of the pin is that of the threaded core for purposes of stress computations.

In the treatment illustrated in FIGS. 1-5, three transfixation pins 60 are employed at separated sites 25 along the limb proximal the injury, the separation being sufficient to ensure there is no interaction between bone stresses from two or more pins. More specifically, the exemplified injury is treated by using stainless steel transfixation pins which are 24 cm long, 9.6 mm in diameter at the head end terminus, have an effective diameter of 8.6 mm, and are threaded 2.5 cm beyond the midline, the thread pitch being 1.6 mm. Sites 25 are separated by 5 cm. Each pin is transfixed through bone 23 and medullary cavity 24 by first drilling a 4.5 mm pilot hole, followed by a 8.73 mm passage, before screwing the pint through the bone. The threaded contact between the thread and bone prevents transverse movement, and passage through the medullary cavity limits stress concentration.

Weight bearing member 36 must be tailored to be compatable with the individual mammal being treated, since this member will bear the weight of the mammal and contact the ground or other bearing surface during ambulation. In general, it must be durable, correctly support the limb, and be readily connectable to the transfixation pin terminii by a rigid link.

In the case of the horse illustrated in the drawings, weight bearing member 36 conveniently includes base 37 and shoe 40. Base 37 is designed to contact the ground, and shoe 40 is adapted to mate to hoof 27. In other embodiments of the invention it is not necessary that a shoe be included to mate with the mammal's foot.

Figure 5:
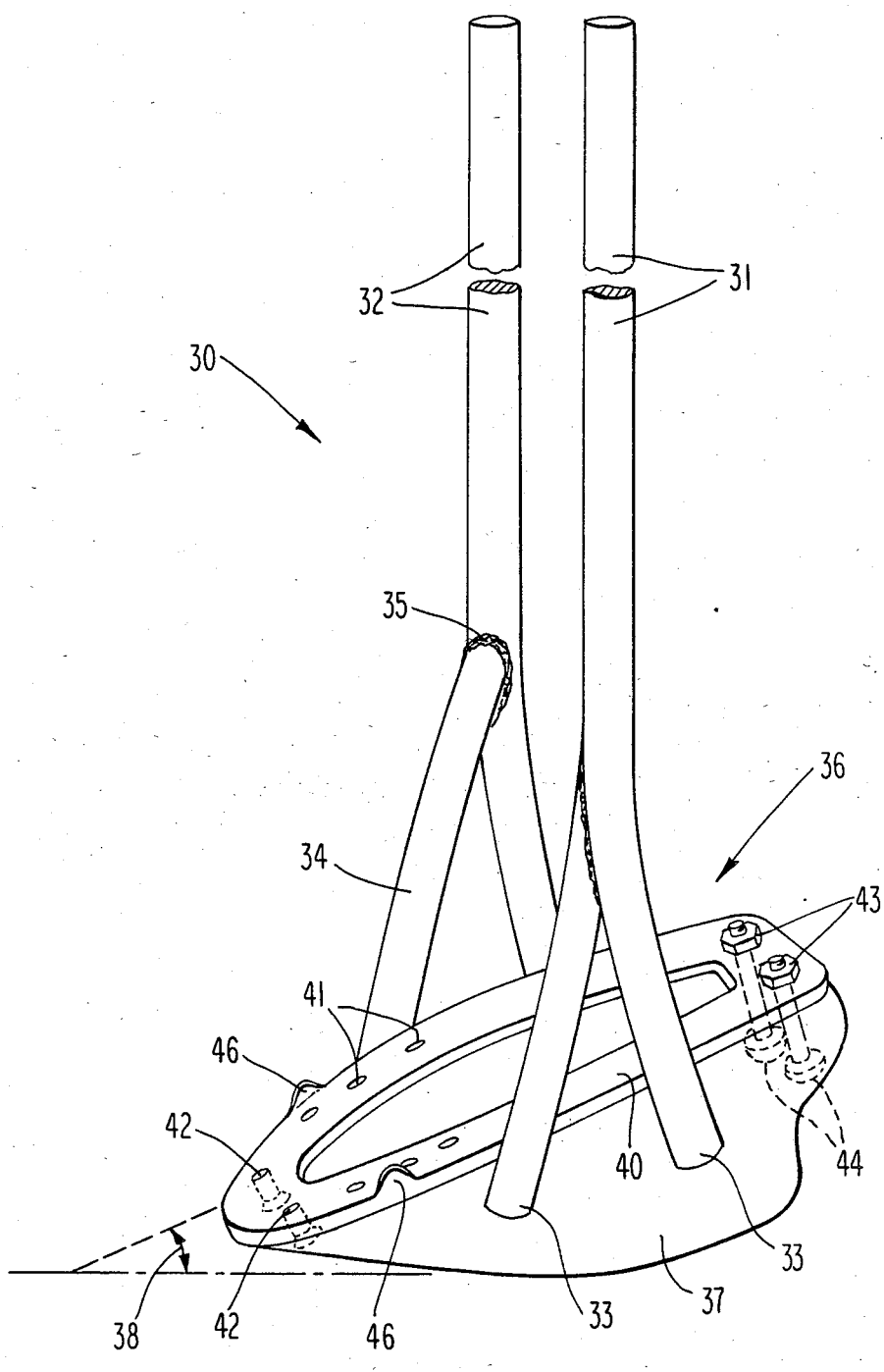
FIG. 5 is a perspective view of the frame assembly employed in the embodiment shown in FIGS. 1–4.

Base 37, seen most clearly in FIGS. 2 and 5, may be a metal casting, e.g., aluminum. As illustrated, the base also holds lateral standard 31, medial standard 32, as well as supporting braces 34. These latter elements, described below, are optional and may be modified or absent, depending upon the specific means employed to connect the weight bearing member to the transfixation pin terminii.

In the event a shoe 40 is employed, it is preferably a bar shoe fitted by a farrier to the horse's hoof prior to application of the skeletal fixator. At the time the shoe is prepared it is advantageous to provide screw holes 42 through the shoe and similar holes to accomodate fastenings 44 at the rear. The base 37 can then be cast to fit the shoe, counterbores in the base being provided to match the fastening holes in the shoe if desired. In preparing base 37, provision can be made to hold the hoof at a therapeutically correct angle with respect to the ground by fixing angle 38, e.g., during casting, and providing means for affixing hoof 27 to base 37.

In the illustrated embodiment bar shoe 40 is nailed to the horse's hoof 27 resting against tabs 46, by means of nails through holes 41 in the shoe. The base 37 is then attached to the shoe, at the rear with bolts 44 and nuts 43, and with screws 42 through holes at the front of the shoe. It will be evident that other types of shoes, including boots which are laced on, rather than nailed to the hoof, can be employed. These devices are detachable, allowing the hoof to be trimmed periodically.

Various means can be employed to connect either or both pin terminii 61 and 62 to weight bearing member 36, including bars or a hemicylindrical sleeve mechanically joining the pin terminii to the weight bearing member with traditional fastening means, e.g., bolts and nuts. Alternatively, a polymerizable organic fluid can be cured in place to adhere to and bridge the pin terminii and weight bearing member. The latter technique offers the advantage of ensuring there are no stress concentrations placed on individual transfixation pins.

An especially attractive means for connecting the pin terminni on each, or either, side of the limb to the weight bearing member is to employ one or more, preferably two, elongated standards, viz., lateral standard 31 and medial standard 32, shown especially in FIG. 5, which are intended to more or less parallel the limb. These standards, which may be of steel rod or tubing, e.g., reinforcing rod used in concrete, are rigidly affixed to weight bearing member 36 by any suitable means, such as a structural adhesive, screws, etc. As an alternative, rod or tubing may be bent at 33 into a U shape and incorporated into base 37. Brace 34 may be similarly constructed, embedded and affixed to a standard at weld 35. The standards may then be rigidly connected by any desired method, e.g., clamps, to the pin terminii on either side of the limb to complete the apparatus. The type of material and size of the standards will be selected depending upon the mammal being treated. In the case of the horse, 0.94 cm diameter steel rod suffices.

Among the various techniques which may be employed to rigidly connect standards 31 and 32 to the transfixation pin terminii, the use of an organic polymer offers a number of advantages, including speed and convenience, as well as avoiding stress concentration. In order to facilitate this technique, lateral tubular mold 51 and medial tubular mold 52 are penetrated by the pin terminii on the lateral and medial sides of the limb, respectively. The diameter of molds 51 and 52 will be chosen to provide the desired strength, depending upon the specific case. In length, the tubing should extend distally as far as possible, e.g., beyond weld 35, and proximally to at least about 5 cm above the most proximal transfixation pin. Any inert, flexible, strong, pliable, penetrable rubber or plastic tubing material will suffice for the molds. One of the useful materials is Armstrong Armaflex tubing, which is available from Wilmington Supply Co., Wilmington, Del. For use in the horse, such tubing with an inside diameter of 6.35 cm and a wall thickness of 1.3 cm is satisfactory. In addition to functioning as a mold, the tubing also acts as a soft cushion to protect the mammal from contact with other parts of the apparatus.

After applying the molds, frame assembly 30, illustrated in FIG. 5, is then slipped up into position with weight bearing member 36 beneath hoof 27 and standards 31 and 32 coaxially encircled by molds 51 and 52, respectively, placing the standards in proximity to the pin terminii within annular voids 53. Weight bearing member 36 is optionally affixed to hoof 27 as described above. The distal ends of the molds are then closed with ties 54, a polymerizable organic fluid 55 is added to fill the molds, and the fluid is polymerized to the rigid organic polymer state. Where maximum strength is required it may be desirable to insert additional reinforcing rods into annular voids 53 before the fluid is added.

In the context of this invention a polymerizable organic fluid includes polymeric melts which solidify on cooling as well as pliant curable prepolymers and extended or filled polymeric or polymerizable monomeric or polymeric materials. Such materials include the class of thermosetting resins. Among this class, epoxy, urethane, phenolic, and polyester resins exhibit cure times and temperatures which make them desirable. The polymerizable organic fluids will be selected from materials which cure at a temperature no higher than about 50 degrees C. The permissible cure time will vary with the mammalian species; in the case of the horse it will not exceed about 30 min. Specifically, the urethane resin known as Isocast Browncast System, available from Isocast Systems, 8899 S.E. Jannsen Road, Clackamas, Oreg. 97015, is very satisfactory.

Figure 6:
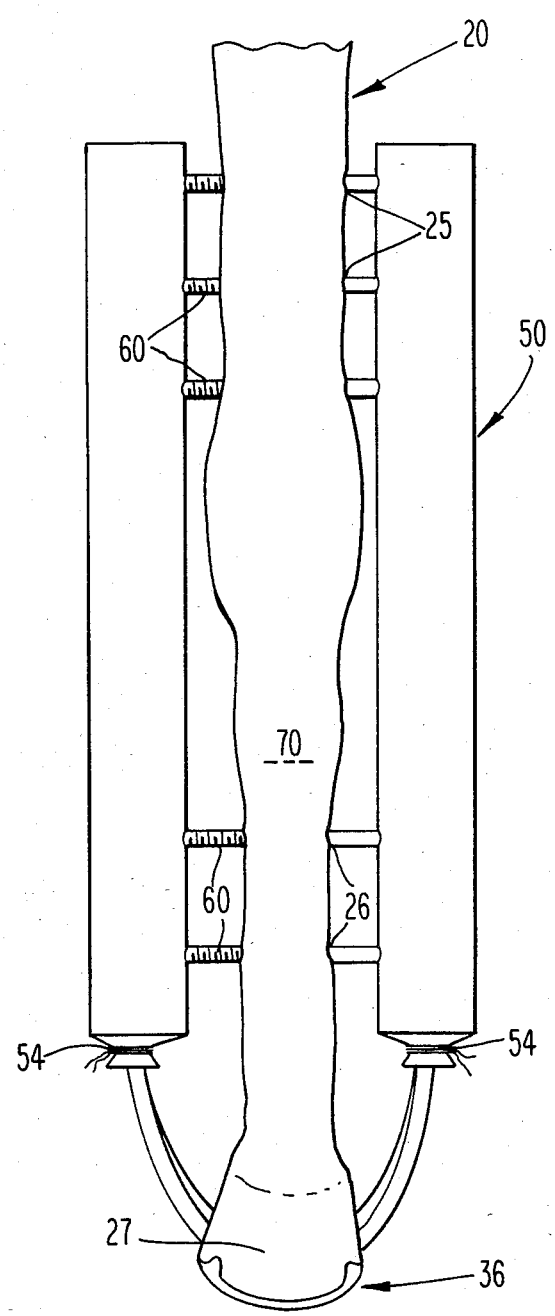
FIG. 6 is a front view of a horse's left foreleg having an injured cannon bone or carpus treated with another embodiment of the external skeletal fixator of this invention.

Many techniques are available to immobilize the limb distal the injury. For example, the weight bearing member may be affixed to the foot of the limb, e.g., by means of a shoe affixed to both the hoof and the weight bearing member as described above. Alternatively, as shown in FIG. 6, additional transfixation pins can be employed to transfix separated sites 26 along the limb distal the injury and terminate beyond the limb. The means used to rigidly connect the transfixation pin terminii proximal the injury can then be used to also rigidly connect the distal pin terminii to the weight bearing member. It may then be unnecessary to affix weight bearing member 36 to hoof 27. Other means for immobilizing the limb distal the injury include slings, wrappings and casts of various kinds, depending upon the type of mammal and the specific injury.

After the apparatus of this invention has been applied to the injured limb, dressing 75 may optionally be added. The apparatus will generally be removed after the injury heals by cutting transfixation pins 60 and freeing the limb distally. Frame assembly 30 can then be slipped away, and the pins unscrewed from the bone.

It will be evident that various modifications of the apparatus and method of use specifically illustrated herein may be desirable, depending upon the mammal and injury being treated. These modifications will be evident to and within the skill of those in the art. The scope of this invention is to be determined from the following claims, not the specifically illustrated embodiments.

We claim:

1. An external skeletal fixator for treating an injured mammalian limb which comprises
    a plurality of transfixation pins which transfix bone at separated sites along the limb proximal the injury and terminate beyond the limb;
    means for rigidly connecting pins terminii to a weight bearing member carried beneath the foot of the limb; together with
    means for immobilizing the limb distal the injury;
    whereby the weight of the mammal is transferred from the limb proximal the injury to said weight bearing member, permitting the mammal to ambulate while the injury heals.

2. The fixator of claim 1 wherein said pins terminii and said weight bearing member are connected by means of a rigid organic polymer.

3. The fixator of claim 1 wherein one or more elongated standards paralleling the limb are rigidly affixed to said weight bearing member, and said standards are rigidly connected to said pin terminii.

4. The fixator of claim 3 wherein tubular molds coaxially encircling said standards provide annular voids penetrated by said pins terminii and containing a rigid organic polymer, thereby connecting said standards to said pins terminii.

5. The fixator of claim 4 wherein said organic polymer is a thermosetting resin.

6. The fixator of claim 5 wherein said thermosetting resin is selected from the group consisting of epoxy, urethane, phenolic, and polyester resins.

7. The fixator of claim 1 wherein said weight bearing member is affixed to the foot of the limb, thereby immobilizing the limb distal the injury.

8. The fixator of claim 1 wherein additional transfixation pins transfix bone at separated sites along the limb distal the injury and terminate beyond the limb, and said means for rigidly connecting said pins terminii proximal the injury to said weight bearing member also rigidly connect said additional pins terminii to said weight bearing member, thereby immobilizing the limb distal the injury.

9. An external skeletal fixator for treating an injured mammalian limb which comprises
    a frame assembly including a pair of elongated rigid standards paralleling the limb and rigidly affixed to a weight bearing member secured beneath the foot of the limb;
    a plurality of transfixation pins which transfix bone at separated sites along the limb proximal the injury and terminate beyond the limb on each side adjacent said standards;
    tubular molds coaxially encircling said srtandards, providing annular voids penetrated by said pins terminii; together with
    a rigid organic polymer contained in said voids rigidly connecting said standards to said pins terminii;
    whereby the weight of the mammal is transferred from the limb proximal the injury to said weight bearing member.

10. A method for treating an injured mammalian limb which comprises transfixing a plurality of transfixation pins through bone at separated sites along the limb proximal the injury to teminate beyond the limb;

providing a weight bearing member beneath the foot of the limb;

connecting said pins terminii rigidly to said weight bearing member; and immobilizing the limb distal the injury;

whereby the weight of the mammal is transferred from the limb proximal the injury to said weight bearing member, permitting the mammal to ambulate while the injury heals.

11. The method of claim 10 which includes connecting said pins terminii to said weight bearing member by means of a rigid organic polymer.

12. The method of claim 10 which includes rigidly affixing one or more elongated standards paralleling the limb to said weight bearing member, and rigidly connecting said standards to said pins terminii.

13. The method of claim 12 which includes coaxially encircling said standards with tubular molds to provide annular voids, penetrating said voids with said pins terminii, adding a polymerizable organic fluid to said molds, and polymerizing said fluid to a rigid organic polymer, thereby connecting said standards to said pins terminii.

14. The method of claim 13 wherein said organic fluid is a thermosetting resin.

15. The method of claim 14 wherein said thermosetting resin is selected from the group consisting of epoxy, urethane, phenolic, and polyester resins.

16. The method of claim 10 which includes affixing the foot of the limb to said weight bearing member, thereby immobilizing the limb distal the injury.

17. The method of claim 10 which includes transfixing additional transfixation pins through bone at separated sites along the limb distal the injury to terminate beyond the limb, and employing said means for rigidly connecting said pins terminii proximal the injury to said weight bearing member to also rigidly connect said additional pins terminii to said weight bearing member, thereby immobilizing the limb distal the injury.

18. An external skeletal fixator kit for treating an injured mammalian limb which comprises a plurality of transfixation pins adapted to transfix bone at separated sites along the limb and terminate beyond the limb;

a frame assembly including both a weight bearing member adapted to be secured beneath the foot of the limb and one or more elongated standards rigidly affixed to said weight bearing member to parallel the limb adjacent said pins terminii; together with means for rigidly connecting said pins terminii to said standards;

whereby application of the fixator to the injured limb allows the weight of the mammal to be transferred from the limb proximal the injury to said weight bearing member, permitting the mammal to ambulate while the injury heals.

19. The kit of claim 18 which includes tubular molds to coaxially encircle said standards and provide annular voids to be penetrated by said pins terminii and contain a rigid organic polymer to connect said pins terminii to said standards.

20. The kit of claim 19 which includes a polymerizable organic fluid to be added to said molds and polymerized to said rigid organic polymer.

* * * * *